(12) United States Patent
Kim et al.

(10) Patent No.: US 12,138,193 B2
(45) Date of Patent: Nov. 12, 2024

(54) FIXING APPARATUS FOR TOES

(71) Applicants: Taeg Sue Kim, Seoul (KR); Dong Ha Kim, Seoul (KR)

(72) Inventors: Taeg Sue Kim, Seoul (KR); Dong Ha Kim, Seoul (KR)

( * ) Notice: Subject to any disclaimer, the term of this patent is extended or adjusted under 35 U.S.C. 154(b) by 306 days.

(21) Appl. No.: 17/869,029

(22) Filed: Jul. 20, 2022

(65) Prior Publication Data
US 2023/0218420 A1 Jul. 13, 2023

(30) Foreign Application Priority Data
Jan. 11, 2022 (KR) .......................... 10-2022-0003691

(51) Int. Cl.
*A61F 5/11* (2006.01)
(52) U.S. Cl.
CPC ...................................... *A61F 5/11* (2013.01)
(58) Field of Classification Search
CPC ............ A61F 5/01–0104; A61F 5/0111; A61F 5/0118; A61F 5/0127; A61F 5/013; A61F 5/019; A61F 5/04; A61F 5/05; A61F 5/058; A61F 5/05841; A61F 5/05858–05875; A61F 5/10; A61F 5/11; A61F 5/37; A61H 1/008; A61B 17/54; A45D 29/00; A45D 29/22
See application file for complete search history.

(56) References Cited

U.S. PATENT DOCUMENTS

| | | | | |
|---|---|---|---|---|
| 2,357,323 A | * | 9/1944 | Goldberg | A61F 5/05866 602/21 |
| 6,932,086 B1 | * | 8/2005 | Hajianpour | A61F 5/05858 128/845 |

FOREIGN PATENT DOCUMENTS

| | | | | |
|---|---|---|---|---|
| CN | 105662686 A | * | 6/2016 | |
| KR | 101659219 B1 | * | 9/2016 | |
| KR | 10-2021-0137963 A | | 11/2021 | |
| WO | WO-2012098552 A1 | * | 7/2012 | ................ A61F 5/11 |

* cited by examiner

*Primary Examiner* — Michelle J Lee
(74) *Attorney, Agent, or Firm* — NKL Law; Jae Youn Kim (57) ABSTRACT

A toe fixing device that is capable of fixing a patient's ingrown toenail to correct the ingrown toenail, without the assistance of the patient or his or her surgeon, to thus allow an adherent composition to be applied to the ingrown toenail of the patient through the free use of both hands of the surgeon. The toe fixing device includes an upper plate reference part having an upper plate, a long movement guide hole piercedly, and a fixing support stand; a lower plate moving part having a lower plate, a fixing hole, a nut, and a moving support stand; and a position fixing part adapted to fix the lower plate moving part movable to the left and right sides along the long movement guide hole of the upper plate reference part to the upper plate reference part.

5 Claims, 6 Drawing Sheets

FIXING APPARATUS FOR TOES

CROSS REFERENCE TO RELATED APPLICATION OF THE INVENTION

The present application claims the benefit of Korean Patent Application No. 10-2022-0003691 filed in the Korean Intellectual Property Office on Jan. 11, 2022, the entire contents of which are incorporated herein by reference.

FIELD OF THE INVENTION

The present invention relates to a toe fixing device that is capable of fixing a patient's ingrown toenail to correct the ingrown toenail, without the assistance of the patient or a surgeon, to thus allow an adherent composition to be applied to the ingrown toenail of the patient through the free use of both hands of the surgeon.

BACKGROUND OF THE RELATED ART

An ingrown toenail is one of foot conditions that develops when one or both sides of the toenail begin to grow into the skin next to it and pierce the flesh. This can lead to inflamed skin and pain. Ingrown toenails usually happen to the big toes.

The causes of ingrown toenail include all of situations where the flesh on one or both sides of a toenail is consistently pressurized against the toenail.

For example, if the corners of the toenail are deeply trimmed by toenail clippers, a piece of toenail not trimmed, which is hidden into the flesh, may curl down and grow into the flesh, and further, if a fungal toenail infection is neglected for a long time, the toenail may be deformed. In addition, when tight footwear is worn for long hours or when obesity or aging develops, the toenail becomes naturally bent seriously. Further, the ingrown toenail may occur by genetic causes.

Initially, the ingrown toenail may cause red skin, swelling, and slight pain on the outside or inside of the big toe, and as the friction of the big toe against the outside occurs frequently, the corresponding area becomes more swollen up to cause pus discharge. Moreover, granulation tissue (a mass of inflammation, blood vessels, and connective tissue) grows to cause the skin around the toenail to fester.

If the ingrown toenail symptoms develop, a bad smell from the toe may be generated, and it is hard to normally walk because of a serious pain.

If walking trouble and infection become serious due to the pain caused by the ingrown toenail, further, a secondary infection disease such as cellulitis (a bacterial skin infection of the deeper layers of skin and the underlying tissue, causing suppurative inflammation) may be caused.

Accordingly, there are proposed correction devices for periodically treating the ingrown toenail to transform an infected toenail shape into a normal toenail shape.

A conventional ingrown toenail correction method is carried out by applying an adherent composition to top of an ingrown toenail through a nail polish type applicator, irradiating ultraviolet rays on the applied adherent composition to contract the adherent composition, and bending the ingrown toenail upward by means of the force generated from the contraction of the adherent composition to thus allow the sides of the toenail growing into the skin to protrude outward. The correction method is repeatedly carried out five times every a given period of time.

In the conventional ingrown toenail correction method, when the adherent composition is applied to top of the ingrown toenail, a patient's big toe has to be fixed by the patient so as to prevent its movements, but the patient's posture for fixing his or her big toe may become unstable to cause the movements of the big toe. In the case of a patient with obesity, he or she may often fail to take the posture for fixing his or her big toe.

Accordingly, while the big toe of the patient is being taken firmly by a surgeon's one hand, the nail polish type applicator has to be held by his or her other hand so as to apply the adherent composition to top of the ingrown toenail of the patient, which undesirably causes the accuracy in application to be reduced.

PRIOR ART DOCUMENT

Patent Literature (Patent Literature 0001) Korean Patent Application Laid-open No. 10-2021-0137963 A

SUMMARY OF THE INVENTION

Accordingly, the present invention has been made in view of the above-mentioned problems occurring in the related art, and it is an object of the present invention to provide a toe fixing device that is capable of fixing a patient's ingrown toenail to correct the ingrown toenail, without the assistance of the patient or a surgeon, to thus allow an adherent composition to be applied to the ingrown toenail of the patient through the free use of both hands of the surgeon.

To accomplish the above-mentioned objects, according to the present invention, there is provided a toe fixing device including: an upper plate reference part having an upper plate, a long movement guide hole piercedly formed in one direction to allow a lower plate moving part to be movable to left and right sides, and a fixing support stand protrudingly extending from one side of the upper plate; the lower plate moving part having a lower plate whose top is located on the underside of the upper plate, a fixing hole piercedly formed on the lower plate at a corresponding position to the long movement guide hole and movable to left and right sides along the long movement guide hole, a nut connected to the underside of the lower plate on which the fixing hole is formed, and a moving support stand protrudingly extending from the other side of the lower plate; and a position fixing part adapted to fix the lower plate moving part movable to the left and right sides along the long movement guide hole of the upper plate reference part to the upper plate reference part and having a bolt passing through the long movement guide hole of the upper plate reference part and fastened to the nut of the lower plate moving part, a handle connected to top end periphery of the bolt and located above the upper plate reference part, and a pressurizing and fixing member extending protrudingly from the lower periphery of the handle so that if the handle rotates in a direction where the bolt is fastened, the pressurizing and fixing member pressurizingly comes into contact with the upper plate.

According to the present invention, desirably, the lower plate moving part may have a forward movement limiting stand vertically bent and extending upward from the front side of the lower plate to thus prevent the upper plate reference part disposed on top thereof from escaping therefrom forward.

According to the present invention, desirably, the lower plate moving part may have a backward movement limiting stand vertically bent and extending upward from the rear side of the lower plate to thus prevent the upper plate reference part disposed on top thereof from escaping therefrom backward.

According to the present invention, desirably, the lower plate moving part may have a floor support stand vertically bent and extending downward from the rear side of the lower plate and coming into contact with the floor so that the lower plate is supported against the floor, without shaking.

According to the present invention, desirably, the handle may have embossed protrusions formed on the side peripheral surface thereof at given intervals so that the handle is firmly taken.

BRIEF DESCRIPTION OF THE DRAWINGS

The above and other objects, features and advantages of the present invention will be apparent from the following detailed description of the embodiments of the invention in conjunction with the accompanying drawings, in which.

DETAILED DESCRIPTION OF THE EMBODIMENTS

Before the present invention is disclosed and described, the present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

In the description, the thicknesses of the lines or the sizes of the components shown in the drawing may be magnified for the clarity and convenience of the description, and for reference numerals, with respect to the same elements, even though they may be displayed in different drawings, such elements use same reference numerals as much as possible. Terms used in this application are used to only describe specific exemplary embodiments and are not intended to restrict the present invention. An expression referencing a singular value additionally refers to a corresponding expression of the plural number, unless explicitly limited otherwise by the context.

As shown in FIGS. 1 to 4A-B, a toe fixing device according to the present invention includes an upper plate reference part 100, a lower plate moving part 200, and a position fixing part 300, so that the toe fixing device is capable of fixing a patient's ingrown toenail to correct the ingrown toenail, without the assistance of the patient or a surgeon, to thus allow an adherent composition to be applied to the ingrown toenail of the patient through the free use of both hands of the surgeon.

First, the upper plate reference part 100 includes an upper plate 110, a long movement guide hole 111 piercedly formed in one direction to move to left and right sides, and a fixing support stand 120 protrudingly extending from one side of the upper plate 110.

In this case, the upper plate 110 is a flat plate and made of a metal such as stainless steel, and the like or a plastic such as polyethylene (PE), polypropylene (PP), and the like.

Further, the fixing support stand 120 is a member for fixing the big toenail of the patient thereto through the position fixing part 300 as will be discussed later in a state of coming into contact with one side of the big toe of the patient having the ingrown toenail, while a moving support stand 230 of the lower plate moving part 200 as will be discussed later is coming into contact with the other side of the big toe of the patient through a sliding movement.

The lower plate moving part 200 includes a lower plate 210 whose top is located on the underside of the upper plate 110, a fixing hole 211 piercedly formed on the lower plate 210 at a corresponding position to the long movement guide hole 111 and movable to left and right sides along the long movement guide hole 111, a nut 220 connected to the underside of the lower plate 210 on which the fixing hole 211 is formed, and a moving support stand 230 protrudingly extending from the other side of the lower plate 210.

In this case, the lower plate 210 is a flat plate and made of a metal such as stainless steel, and the like or a plastic such as polyethylene (PE), polypropylene (PP), and the like.

When the fixing hole 111 moves to the left or right side along the long movement guide hole 111 according to the size of the big toe of the patient, the moving support stand 230 protrudingly extending from the lower plate 210 moves to the left or right side to come into contact with the other side of the big toe of the patient, so that when the position fixing part 300 as will be discussed later is fixed, the moving support stand 230 and the fixing support stand 120 serve to fix both sides of the big toe of the patient thereto, thereby allowing an adherent composition to be applied to top of the ingrown toenail of the patient through the free use of both hands of the surgeon.

Further, the lower plate moving part 200 has members for preventing the upper plate reference part 100 disposed on top thereof from escaping therefrom forward or backward at the time when the fixing hole 111 moves to the left or right side along the long movement guide hole 111 according to the size of the big toe of the patient.

First, the lower plate moving part 200 has a forward movement limiting stand 240 vertically bent and extending upward from the front side of the lower plate 210 to thus prevent the upper plate reference part 100 disposed on top thereof from escaping therefrom forward during the movement of the upper plate reference part 100.

Like this, the vertically bent forward movement limiting stand 240 is disposed along the front side of the lower plate 210 or limitedly located on a portion of the moving support stand 230.

In this case, the height of the moving support stand 230 of the lower plate 210 is increased upward by means of the vertically bent forward movement limiting stand 240, and accordingly, an upper plate connection stand 130 is disposed between the fixing support stand 120 and the upper plate 110 of the upper plate reference part 100 and vertically bent upward, while having a length of the forward movement limiting stand 240, so that when the moving support stand 230 and the fixing support stand 120 fixedly come into contact with both sides of the big toe of the patient, they have the same height as each other, thereby providing excellent toe fixing performance.

Further, the lower plate moving part 200 has a backward movement limiting stand 250 vertically bent and extending upward from the rear side of the lower plate 210 to thus prevent the upper plate reference part 100 disposed on top thereof from escaping therefrom backward during the movement of the upper plate reference part 100.

Like this, the vertically bent backward movement limiting stand 250 is disposed along the rear side of the lower plate 210, and otherwise, vertically bent backward movement limiting stands 250 are limitedly located on both sides of the rear side of the lower plate 210, respectively. In this case, it is desirable that the vertically bent backward movement limiting stands 250 are limitedly located on both sides of the rear side of the lower plate 210, respectively. This is because a floor support stand 260 as will be discussed later extends from the central portion of the rear side of the lower plate 210, and the floor support stand 260 will be explained in detail below.

Further, the toe fixing device according to the present invention has a member adapted to fix the lower plate moving part 200 to the floor to prevent the lower plate 210 from shaking, so that the adherent composition can be accurately applied to top of the ingrown nail of the patient from a nail polish type applicator.

To do this, the floor support stand 260 is vertically bent and extending downward from the rear side of the lower plate 210 of the lower plate moving part 200 and comes into contact with the floor.

In this case, the floor support stand 260 is bent from the central portion of the rear side of the lower plate 210 of the lower plate moving part 200, and the length of the floor support stand 260 coming into contact with the floor is longer than the width of the lower plate 210, so that in a state where the big toe of the patient is fixed, the movement of the big toe of the patient can be limited to the maximum, that is, the big toe of the patient cannot move.

Further, the backward movement limiting stands 250 are located on both sides of the rear side of the lower plate 210 of the lower plate moving part 200, respectively, thereby allowing the floor support stand 260 to fixedly come into contact with the floor and preventing the upper plate reference part 100 from escaping backward during the sliding movement of the upper plate reference part 100.

The position fixing part 300 serves to fix the lower plate moving part 200 movable to the left and right sides along the long movement guide hole 111 of the upper plate reference part 100 to the upper plate reference part 100 and includes a bolt 310 passing through the long movement guide hole 111 of the upper plate reference part 100 and fastened to the nut 220 of the lower plate moving part 200, a handle 320 connected to top end periphery of the bolt 310 and located above the upper plate reference part 100, and a pressurizing and fixing member 330 extending protrudingly from the lower periphery of the handle 320 so that if the handle 320 rotates in a direction where the bolt 310 is fastened, the pressurizing and fixing member 330 pressurizingly comes into contact with the upper plate 110.

In this case, the handle 320 has embossed protrusions 321 formed on the side peripheral surface thereof at given intervals so that while the big toe of the patient is being fixed by the surgeon, the handle 320 can be firmly taken by the surgeon by means of the frictional forces caused by the embossed protrusions 321.

Figure 1:
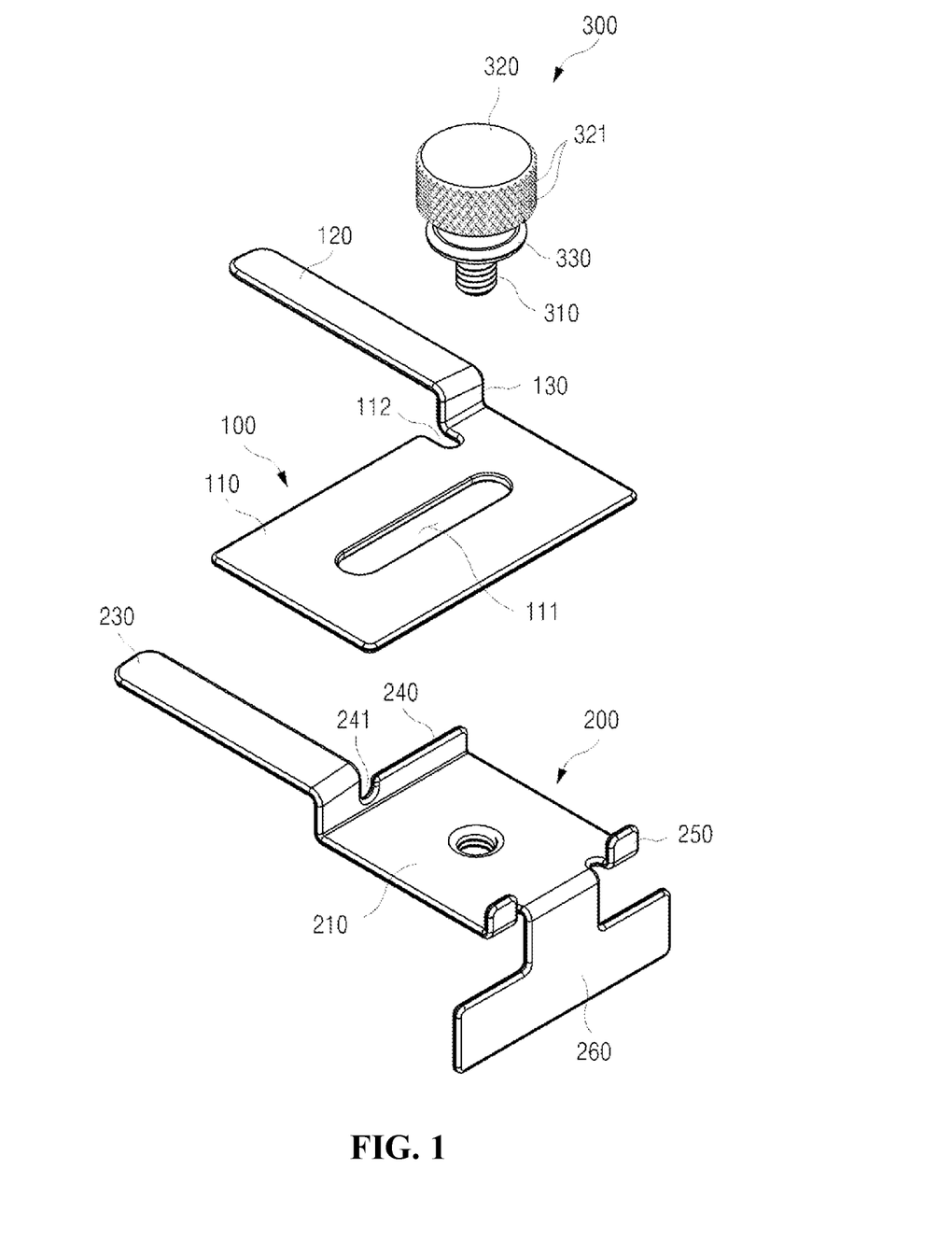
FIG. 1 is an exploded perspective view showing a toe fixing device according to the present invention.
Figure 2:
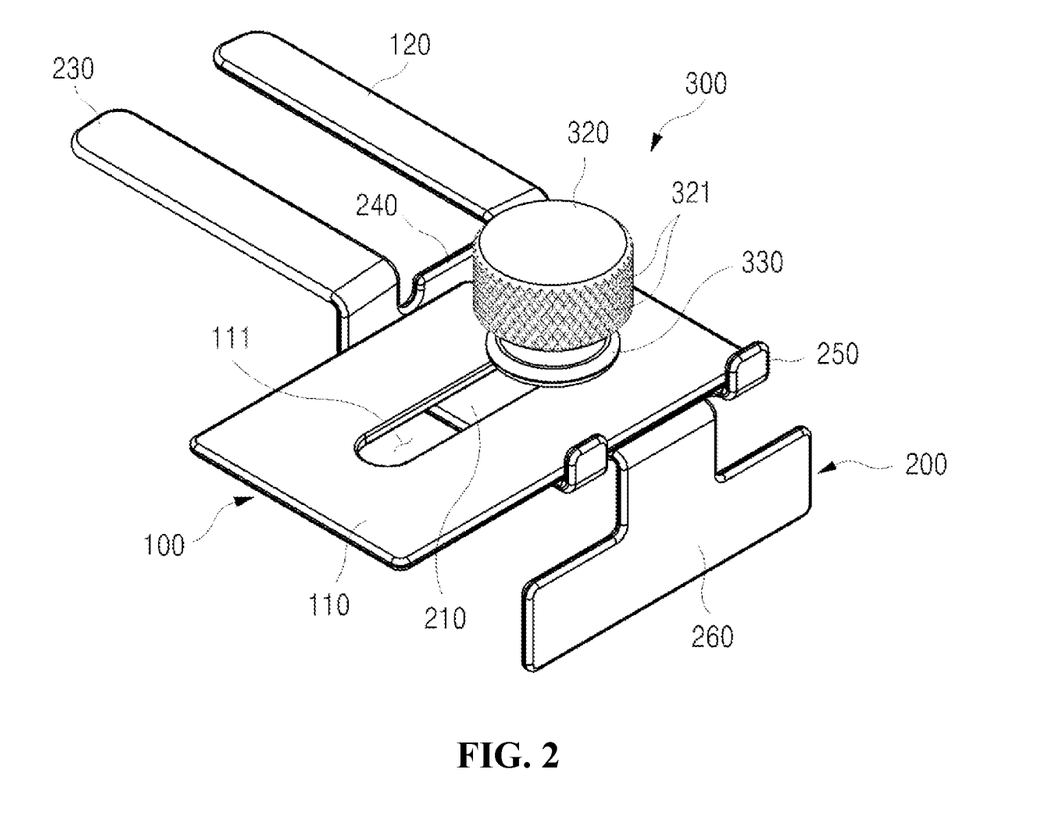
FIGS. 2 and 3 are perspective views showing the toe fixing device according to the present invention.
Figure 3:
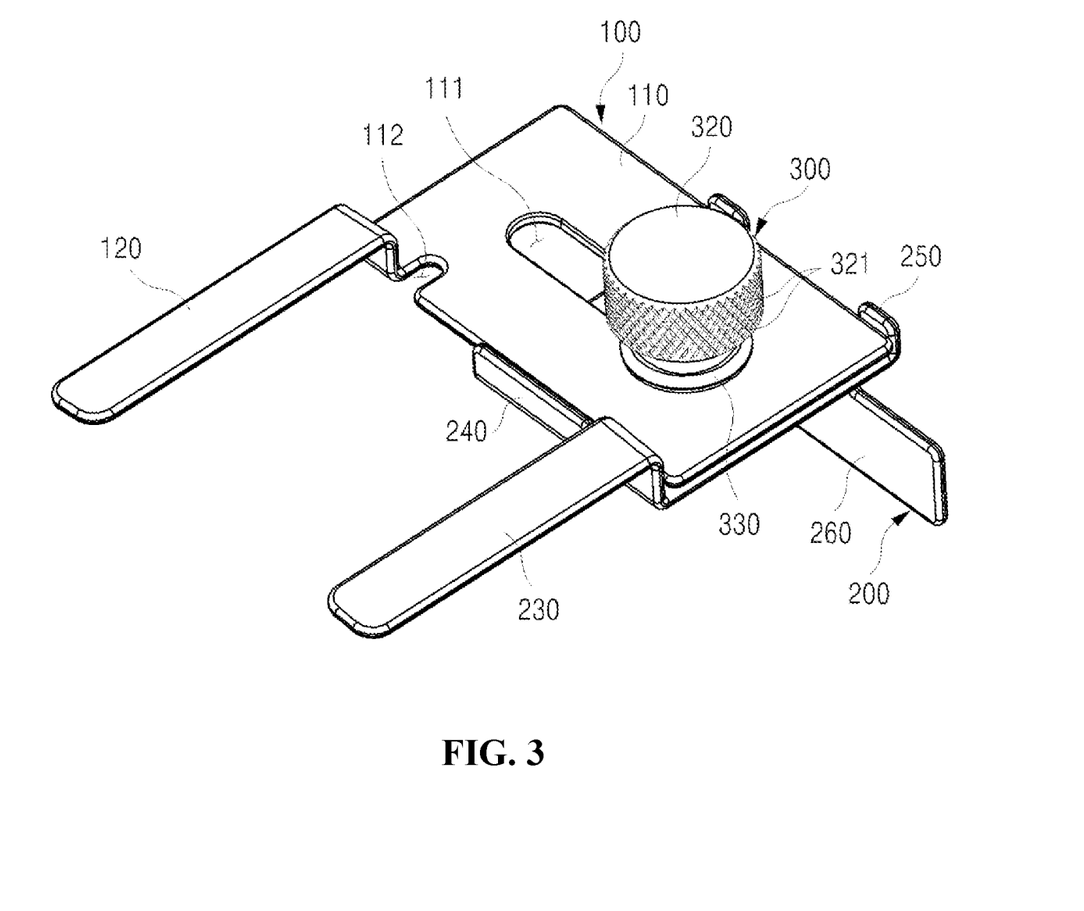
Figure 4A:
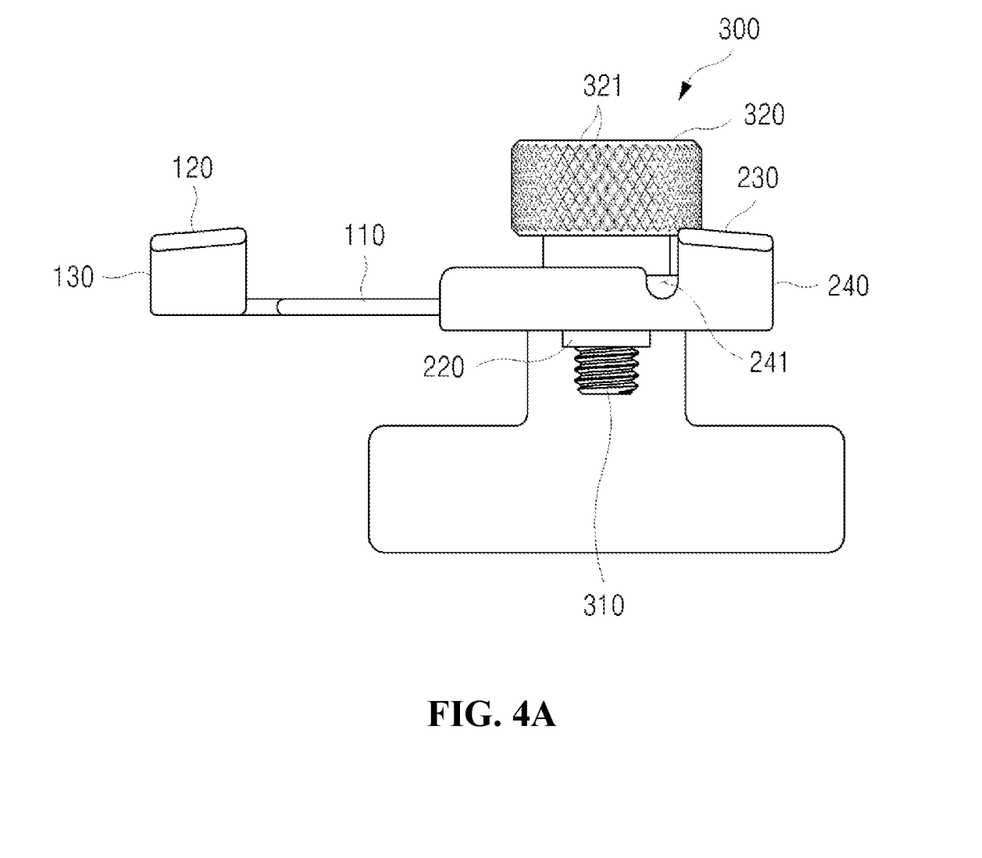
FIGS. 4A and 4B are side views showing states in which a fixing support stand and a moving support stand of the toe fixing device according to the present invention are open from each other to the maximum and close to each other to the maximum.
Figure 4B:
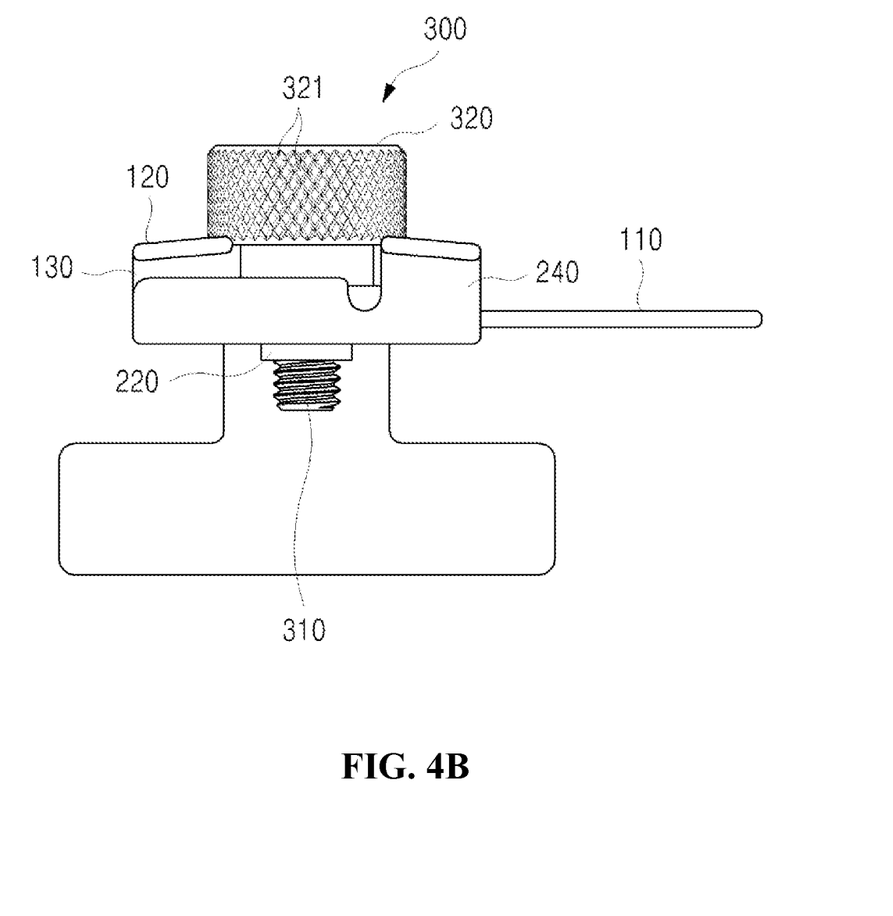
Figure 5:
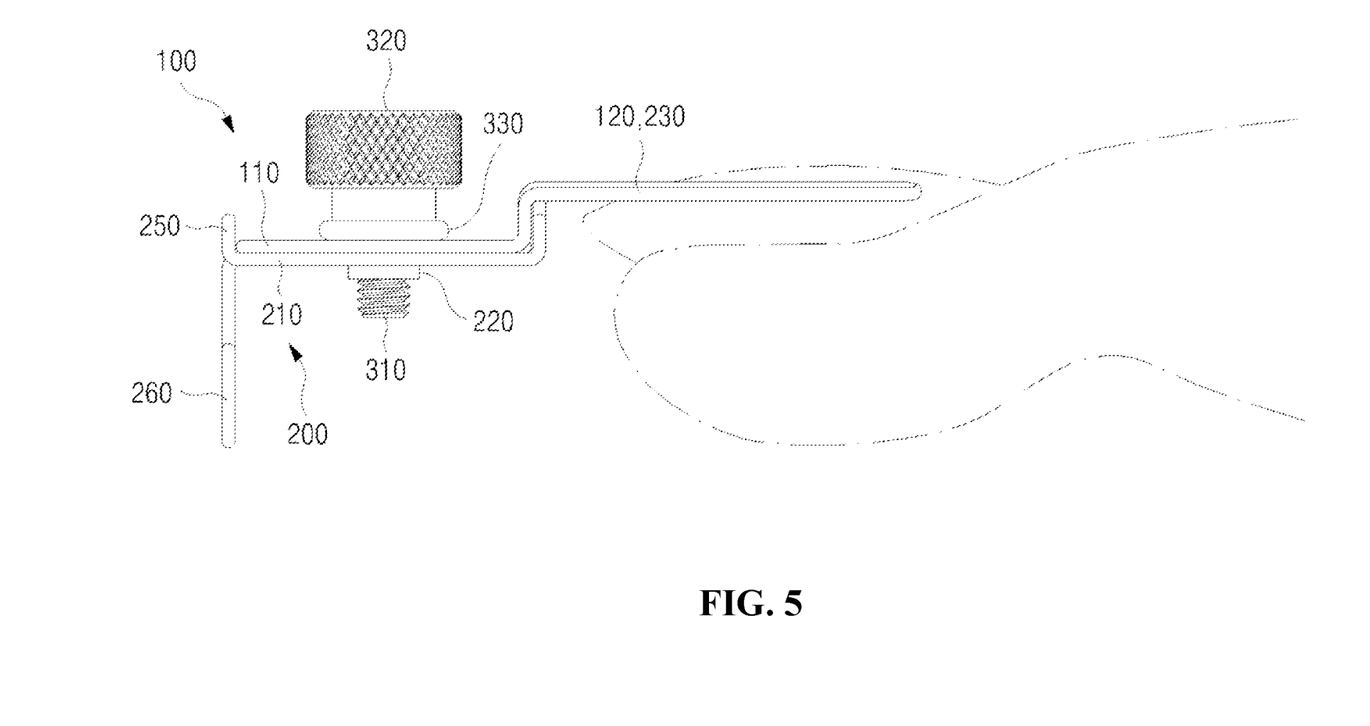
FIG. 5 is a side view showing a process for fixing a patient's ingrown toenail through the toe fixing device according to the present invention.

Under the above-mentioned configuration, a process of fixing the big toe of the patient in which the ingrown toenail occurs through the toe fixing device according to the present invention will be explained with reference to FIG. 5.

First, the handle 320 of the position fixing part 300 rotates in a fixing releasing direction by the surgeon to thus release the coupling state between the lower plate moving part 200 and the upper plate reference part 100, so that the lower plate moving part 200 slidingly moves to the left and right sides with respect to the upper plate reference part 100.

After that, the big toe of the patient in which the ingrown toenail occurs is located between the moving support stand 230 extending from the lower plate 210 of the lower plate moving part 200 and the fixing support stand 120 extending from the upper plate reference part 100.

Next, the floor support stand 260 extending from the lower plate 210 of the lower plate moving part 200 comes into contact with the floor to thus allow the lower plate 210 of the lower plate moving part 200 to be fixed, without shaking. In this case, the fixing support stand 120 of the upper plate reference part 100 comes into contact with one side of the big toe of the patient in which the ingrown toenail occurs.

After that, if the handle 320 of the position fixing part 300 is held by the surgeon and moves to the right side, the lower plate 210 screw-fastened to the handle 320 interlocks with the handle 320 and moves to the right side. In this case, the bolt 310, which is piercedly located in the long movement guide hole 111 of the upper plate 110, moves to the right side along the long movement guide hole 111.

Further, the bolt 310 moves to the right side until the other side of the big toe of the patient comes into contact with the side of the moving support stand 230 of the lower plate 210.

Next, if the handle 320 of the position fixing part 300 rotates in a locking direction by the surgeon, the bolt 310 connected to the handle 320 rotates in the locking direction to thus move the handle 320 downward, and in this case, the handle 320 moves until it cannot move downward anymore by means of the pressurization of the pressurizing fixing member 330 against the upper plate 110.

As a result, both sides of the big toe of the patient come into contact with the moving support stand 230 of the lower plate 210 and the fixing support stand 120 of the upper plate 110, respectively, and are thus fixed.

After that, the nail polish type applicator is taken by the surgeon's one hand and controlled to apply the adherent composition to be accurately applied to top of the big toenail of the patient. In this case, the adherent composition is applied by given application times for given application time.

Next, if the application of the adherent composition is finished, the toe fixing device fixed to the big toe of the patient is released in the reverse order to the order mentioned above.

As described above, the toe fixing device according to the present invention can fix the big toe of the patient in which the ingrown toenail occurs so as to correct the ingrown toenail, without the assistance of the patient or the surgeon, to allow the adherent composition to be applied to the ingrown toenail of the patient through the free use of both hands of the surgeon.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

| Explanations of Reference Numerals in the Drawings | |
|---|---|
| 100: Upper plate reference part | 111: Long movement guide hole |
| 110: Upper plate | 120: Fixing support stand |
| 130: Upper plate connection stand | 200: Lower plate moving part |
| 210: Lower plate | 211: Fixing hole |
| 220: Nut | 230: Moving support stand |
| 240: Forward movement limiting stand | 250: Backward movement limiting stand |
| 260: Floor support stand | 300: Position fixing part |
| 310: Bolt | 320: Handle |
| 321: Embossed protrusion | 330: Pressurizing and fixing member |

What is claimed is:

1. A toe fixing device comprising:
an upper plate reference part having an upper plate, a long movement guide hole piercedly formed in one direction to allow a lower plate moving part to be movable to left and right sides, and a fixing support plate protrudingly extending from one side of the upper plate;
the lower plate moving part having a lower plate whose top is located on an underside of the upper plate, a fixing hole piercedly formed on the lower plate at a corresponding position to the long movement guide hole and movable to left and right sides along the long movement guide hole, a nut connected to an underside of the lower plate on which the fixing hole is formed, and a moving support plate protrudingly extending from another side of the lower plate; and
a position fixing part adapted to fix the lower plate moving part movable to the left and right sides along the long movement guide hole of the upper plate reference part to the upper plate reference part and having a bolt passing through the long movement guide hole of the upper plate reference part and fastened to the nut of the lower plate moving part, a handle connected to a top end periphery of the bolt and located above the upper plate reference part, and a pressurizing and fixing member extending protrudingly from a lower periphery of the handle so that when the handle rotates in a direction where the bolt is fastened, the pressurizing and fixing member pressurizingly comes into contact with the upper plate; and
wherein, in use, a toe is configured to be directly secured between a floor and an underside of each of the fixing support plate and moving support plate to fix the toe.

2. The toe fixing device according to claim 1, wherein the lower plate moving part has a forward movement limiting stand vertically bent and extending upward from a front side of the lower plate to thus prevent the upper plate reference part disposed on top thereof from escaping therefrom forward.

3. The toe fixing device according to claim 1, wherein the lower plate moving part has a backward movement limiting stand vertically bent and extending upward from a rear side of the lower plate to thus prevent the upper plate reference part disposed on top thereof from escaping therefrom backward.

4. The toe fixing device according to claim 1, wherein the lower plate moving part has a floor support stand vertically bent and extending downward from a rear side of the lower plate to come into contact with the floor so that the lower plate is supported against the floor, without shaking.

5. The toe fixing device according to claim 1, wherein the handle has embossed protrusions formed on a side peripheral surface thereof at given intervals.

* * * * *